(12) United States Patent
Baek et al.

(10) Patent No.: US 10,524,672 B2
(45) Date of Patent: Jan. 7, 2020

(54) DIASTOLIC BLOOD PRESSURE MEASUREMENT CALIBRATION

(71) Applicant: Capsule Technologies, Inc., San Diego, CA (US)

(72) Inventors: David Boettcher Baek, San Diego, CA (US); Lars Lading, Roskilde (DK)

(73) Assignee: CAPSULE TECHNOLOGIES, INC., San Diego, CA (US)

( * ) Notice: Subject to any disclaimer, the term of this patent is extended or adjusted under 35 U.S.C. 154(b) by 647 days.

(21) Appl. No.: 15/188,324

(22) Filed: Jun. 21, 2016

(65) Prior Publication Data

US 2017/0360313 A1   Dec. 21, 2017

(51) Int. Cl.
*A61B 5/02* (2006.01)
*A61B 5/021* (2006.01)
*A61B 5/00* (2006.01)

(52) U.S. Cl.
CPC .......... *A61B 5/02116* (2013.01); *A61B 5/002* (2013.01); *A61B 5/0022* (2013.01); *A61B 5/681* (2013.01); *A61B 5/6826* (2013.01); *A61B 5/7282* (2013.01); *A61B 5/6825* (2013.01); *A61B 5/6831* (2013.01); *A61B 2560/0223* (2013.01); *A61B 2560/0242* (2013.01)

(58) Field of Classification Search
CPC ....... A61B 5/021; A61B 5/00; A61B 5/02116; A61B 5/002; A61B 5/0022; A61B 5/681; A61B 5/6826; A61B 8/04; A61B 5/02108; A61B 5/02241; A61B 5/02422; A61B 5/0295; A61B 5/7282; A61B 5/6824; A61B 2560/0242; A61B 2560/0223; A61B 5/6825; A61B 5/6831; A61B 8/488; A61B 5/0263; A61B 5/1114; A61B 5/1116

See application file for complete search history.

(56) References Cited

U.S. PATENT DOCUMENTS

| | | |
|---|---|---|
| 6,939,305 B2 | 9/2005 | Flaherty et al. |
| 7,390,301 B2 | 6/2008 | Skrabal et al. |
| 7,674,231 B2 | 3/2010 | McCombie et al. |
| 8,672,854 B2 | 3/2014 | McCombie et al. |

(Continued)

OTHER PUBLICATIONS

International Search Report and Written Opinion—PCT/US2017/033491—ISA/EPO—dated Aug. 31, 2017.

*Primary Examiner* — Eric J Messersmith
(74) *Attorney, Agent, or Firm* — Kilpatrick Townsend & Stockton LLP

(57) ABSTRACT

Various embodiments include methods and devices for measuring blood pressure. Various embodiments may include receiving, from one or more arterial measurement sensors, a pulse waveform representing arterial pressure as a function of time for each pulse of a series of blood pressure pulses. The series of blood pressure pulses may be correlated to arterial distension at a measurement location of the arterial measurement sensors on a subject's body. One or more elevations of the measurement location may be received from one or more elevation sensors. At least one pulse in the series of pulses may be identified that represents a transitional pulse based on one or more characteristics of the at least one pulse. A diastolic blood pressure may be determined based on the at least one identified transitional pulse and elevation measurements that correspond to the one identified pulse.

29 Claims, 6 Drawing Sheets

(56) References Cited

U.S. PATENT DOCUMENTS

| | | | |
|---|---|---|---|
| 2005/0004477 A1* | 1/2005 | Friedman | A61B 5/021 600/485 |
| 2007/0167844 A1* | 7/2007 | Asada | A61B 5/022 600/485 |
| 2009/0287097 A1 | 11/2009 | Lowe | |
| 2010/0298717 A1 | 11/2010 | Parfyonov et al. | |
| 2011/0009718 A1* | 1/2011 | Gavish | A61B 5/021 600/310 |
| 2015/0327784 A1 | 11/2015 | Lading et al. | |
| 2016/0262639 A1* | 9/2016 | Ukawa | A61B 5/02116 |

* cited by examiner

DIASTOLIC BLOOD PRESSURE MEASUREMENT CALIBRATION

BACKGROUND

Devices for measuring cardiovascular properties suffer from the problem that the measurement itself interferes with the state of the subject, thereby leading to erroneous results. In addition, current cuff-based methods may impart a significant physiological impact. In current cuff-based methods, the systolic blood pressure is obtained by completely or at least substantially constricting an artery, which in most cases is the brachial artery in the upper arm. Such constriction of the artery affects pulse pressure propagation and pulse pressure shapes, which may only be tolerated in the peripheral system. Further, the diastolic pressure is derived from measurements obtained when the transmural pressure (pressure difference between the outside and the inside of an artery) is close to zero, which implies those measurements are made under conditions that are far from normal.

In addition, traditional methods based on inflatable cuffs and measurements performed in a clinical environment may have psychological effects causing changes in a patient's blood pressure. For example, the psychological effects of being in clinical environment may cause an elevation in the patient's blood pressure. The phenomenon is commonly called "white coat syndrome" or "white coat hypertension." In an additional example, a patient's blood pressure may be elevated during normal daily activities but not in a clinical setting. This phenomenon is commonly called "masked hypertension."

SUMMARY

Various embodiments include methods and devices for measuring blood pressure. Various embodiments may include receiving, from one or more arterial measurement sensors, a pulse waveform representing arterial pressure as a function of time for each pulse of a series of blood pressure pulses, wherein the series of blood pressure pulses may be correlated to arterial distension at a measurement location of the one or more arterial measurement sensors on a subject's body, receiving, from one or more elevation sensors, one or more elevations of the measurement location, identifying, by a processor, at least one pulse in the series of blood pressure pulses that represents a transitional pulse based on one or more characteristics of the at least one pulse, and determining, by the processor, a calibrated diastolic blood pressure based on the at least one identified pulse and at least one elevation from the one or more elevations that correspond to the at least one identified pulse. In some embodiments, the series of blood pressure pulses may be measured while a limb of the subject is raised from at or below a heart level of the subject to above the heart level.

In some embodiments, one or more characteristics of the at least one pulse may include amplitude, pulse shape, or any combination thereof. In some embodiments, identifying at least one pulse in the series of blood pressure pulses that represents the transitional pulse may include identifying the at least one pulse in the series of blood pressure pulses with an amplitude that is a predetermined fraction of a maximum pulse amplitude. In some embodiments, identifying at least one pulse in the series of blood pressure pulses that represents the transitional pulse may include comparing individual pulse shapes of individual pulses in the series of blood pressure pulses to a mean pulse shape of the series of blood pressure pulses and identifying the transitional pulse within the series of blood pressure pulses from a pulse shape deviation from the mean pulse shape by a predetermined percentage. In some embodiments, identifying at least one pulse in the series of blood pressure pulses that represents the transitional pulse may include identifying an individual pulse within the series of blood pressure pulses having an oscillatory pulse shaped diastolic tail immediately preceded by an earlier pulse having a near exponential decay shaped diastolic tail. In some embodiments, identifying at least one pulse in the series of blood pressure pulses that represents the transitional pulse may include identifying an individual pulse within the series of blood pressure pulses having a kink in a lowest segment of a diastolic tail of the individual pulse, wherein the kink meets a threshold deviation from a predetermined pulse shape.

In some embodiments, the one or more arterial measurement sensors may include a non-interfering measuring device configured to measure changes in distension of an artery without interfering with the arterial pressure at the measurement location during the series of blood pressure pulses. Non-interfering may also include embodiments that apply a constant counter pressure, below a diastolic pressure of the subject, at the measurement location during the series of blood pressure pulses. In some embodiments, the one or more elevation sensors may include an elevation sensor selected from the group consisting of an inertial sensor, a barometer, a magnetic near-field device, a visual inertial odometer, a global navigation satellite system (GNSS) based sensor, and a wireless local area network (WLAN) based sensor.

Further embodiments include a blood pressure measuring device having one or more arterial measurement sensors, one or more elevation sensors, and a processor configured to perform operations of the methods summarized above. Further embodiments include a blood pressure measuring device having one or more arterial measurement sensors, one or more elevation sensors, and means for performing functions of the methods summarized above. Further embodiments include a processor-readable storage medium on which is stored processor-executable instructions configured to cause a processor of a blood pressure measuring device to perform operations of the methods summarized above.

BRIEF DESCRIPTION OF THE DRAWING

The accompanying drawings, which are incorporated herein and constitute part of this specification, illustrate various embodiments of the claims, and together with the general description given above and the detailed description given below, serve to explain the features of the claims.

DETAILED DESCRIPTION

Figure 1A:
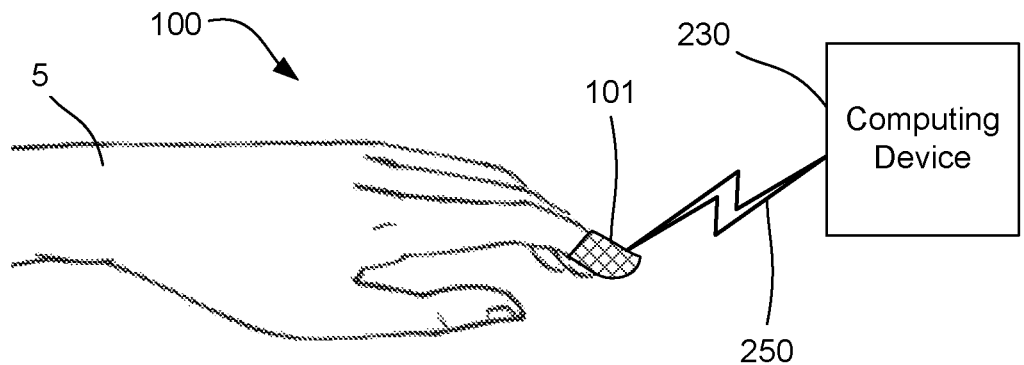
FIG. 1A is a schematic diagram of a non-interfering blood pressure measuring device according to various embodiments.

Various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims.

Various embodiments include methods for calibrating a blood pressure measuring device by determining a calibrated diastolic blood pressure from arterial distension measurements taken under known pressure conditions corresponding to when the transmural pressure is or approaches zero. In some embodiments, the known pressure conditions may include a constant applied counter pressure and controlled changes in hydrostatic pressure. The hydrostatic pressure may be changed by adjusting the elevation of the measurement site. The hydrostatic pressure in a limb at the site of measurements, as well as a relatively minor counter pressure applied to the limb, may provide known or predictable pressure conditions that may be used to manipulate the transmural pressure to enable determining the calibrated diastolic blood pressure.

The internal blood pressure of an artery at a measurement location generally equals any external pressure, such as a minor applied counter pressure, plus a counteracting pressure from the arterial wall (i.e., internal blood pressure equals counter pressure plus transmural pressure). In addition, the internal blood pressure may represent the calibrated diastolic blood pressure, plus pressure from hydrostatic pressure. Under conditions in which the transmural pressure is or approaches zero, a characteristic change in the diastolic part of a pulse waveform occurs. By adjusting either or both of an applied counter pressure and the hydrostatic pressure until that characteristic change in the diastolic part of a pulse waveform is observed, an calibrated diastolic blood pressure may be determined by knowing the applied counter pressure and hydrostatic pressure resulting in the zero transmural pressure conditions. Thus, a blood pressure measuring device implementing various embodiments may determine the calibrated diastolic blood pressure by adjusting applied counter pressure and hydrostatic pressure while monitoring the diastolic part of a pulse waveform and noting applied counter pressure and hydrostatic pressure when the diastolic pulse waveform has the characteristic shape exhibited in zero transmural pressure conditions.

Various embodiments use non-invasive techniques that identify dynamic changes in arterial distension from a pulse waveform representing arterial pressure measurement values over time during each pulse. Characteristic shapes may be identified within at least a diastolic part of a pulse waveform that correlate to conditions in which the transmural pressure is approximately zero (i.e., when arterial wall tension is or approaches zero). Under such conditions, at least a diastolic part of the calibrated diastolic blood pressure may be determined for calibrating a blood pressure measuring device.

As used herein, the term "pulse waveform" refers to a graphic representation of arterial pressure as a function of time for each pulse of a series of blood pressure pulses correlated to an arterial distension at a measurement location on a limb of a subject. The pulse waveform of each pulse is characterized by a shape that may be analyzed and compared to one or more predetermined shapes. As used herein, the terms "pulse" or "blood pressure pulse" are used interchangeably to refer to the regular arterial distension of an artery caused by local pressure increase that occurs with the ejection of blood into the arterial system by the contractions of the heart. As used herein, the term "transitional pulse" refers to a pulse reflecting a notable transition from one state of an artery to another.

As used herein, the term "pulse pressure" refers to the difference between systolic and diastolic pressures, which changes during the time from one heart beat to the next. This value is generally not affected by local changes in the hydrostatic pressure in the peripheral regions of the body of the subject, as long as the transmural pressure remains positive.

As used herein, the term "transmural pressure" refers to the pressure difference between the pressure inside an artery and directly outside the artery at a specific location in a specific artery. The transmural pressure will depend on the hydrostatic pressure, which may be influenced by the height of the measurement location. For example when a measuring device is attached to the wrist of a subject, moving the wrist slowly up and down will cause significant changes in the transmural pressure measured at the measuring location, while the pulse pressure will be relatively unaffected by slow up and down motion of the wrist. Without an externally applied counter pressure (e.g., inward pressure from a cuff, adhesive bandage, or other externally applied element), the transmural pressure may be presumed to be approximately equal to the blood pressure.

The terms "calibrated blood pressure" or "calibrated diastolic blood pressure" are used herein to define the actual pressure in an artery at a specific location and at a particular time. In various embodiments, a hydrostatic pressure, together with a minor counter pressure, may equal a calibrated diastolic blood pressure during conditions in which a transmural pressure is equal to or approaches zero. In contrast, the term "blood pressure" is used herein as a general term to refer to a pressure in the arterial system of the subject. For the sake of this specification, the transmural pressure, the pulse pressure, and the calibrated blood pressure are all considered "blood pressures." For example, devices that measure the transmural pressure at a specific location and devices that measure the pulse pressure may be used to measure and/or estimate blood pressure.

As used herein, the expression "constant pulse rate" refers to a pulse rate that over a period of several heartbeats does not change significantly (e.g., not more than 10%). In this respect, a beat-to-beat variation may be as high as 50% and still be considered a constant pulse rate. Thus, an average of the pulse rate over a certain amount of time may be used. For example, a pulse rate measured over 30-60 seconds may be considered constant if variations over that period are below 10%. Alternatively, an upper limit of variation may be used, such as 5%, 2%, or 1%. As a further alternative, a moving average over a certain amount of time (e.g., 1 minute) may be used for calculating pulse rate and determining whether the pulse rate is constant. As yet a further alternative, a limit on the maximum amount of change in a moving average of the pulse rate in a certain amount of time may be used. This may be related to the derivative/slope of the moving average of the pulse rate.

As used herein, the term "measuring device" refers to a physical apparatus for taking measurements of biometric and/or physical changes to a subject. The measuring device may be a structure that can be worn by the subject or a structure near or adjacent the subject, such as on a fixture (e.g., furniture, sports equipment, automobile fixtures, etc.). In contrast, the term "sensor" generally refers to a device that responds to a physical stimulus (as heat, light, sound, pressure, magnetism, or a particular motion) and transmits a resulting impulse (as for measurement or operating a control). A sensor may measure changes in position, size, and/or composition, such as within an organ or a portion of a body. For example, the term "arterial measurement sensor" more specifically refers to a component of the measuring device, which performs the actual measurement of a physical characteristic of an artery of the subject, such as fluctuations in blood flow and/or the cross-sectional area of an artery. Similarly, the term "elevation sensor" more specifically refers to a component configured to detect an elevation or changes in an elevation at a measurement location. An elevation sensor may output one or more elevation indicators. As used herein, the term, "elevation indicator" refers to a gauge of position, movement, proximity, speed, acceleration, and/or other measurement from which an elevation or change in elevation may be determined. An elevation sensor may include a 3D inertial sensor, such as an accelerometer, in which elevation changes may be inferred from integration of the accelerometer output. Other examples of elevation sensors include a barometer, a magnetic near-field device, a visual inertial odometer, a GNSS based sensor, a WLAN based sensor (e.g., WWAN, Bluetooth, or Wi-Fi), visible light communication (VLC) or any other type of sensor configured to measure the elevation or a change in elevation of a measurement location. The measuring device may include an arterial measurement sensor, an elevation sensor, and computing devices for processing signals from the arterial measurement sensor, the elevation sensor, and/or communicating with external equipment. The arterial measurement sensor and/or the elevation sensor do not have to directly contact an artery, but may be placed on a skin surface above or near the artery.

Any of a wide variety of measuring devices may be used with the various embodiments. For example, a measuring device may be configured to be wearable, such as in the form of, or incorporated into, a patch, a finger sleeve (such as the non-interfering blood pressure measuring device 100 shown in FIGS. 1A and 1B), a wrist cuff, a finger ring, a band of a wrist watch, a back case of a wrist watch, and/or another form of apparel (i.e., clothing that includes an embodiment of a measuring device). However, the various embodiments may be used with measuring devices that are not worn by a subject, but are configured to place the sensor against the skin of the subject. For example, a measuring device may be incorporated into safety belts, steering wheels, armrests, seats and other structures in an automobile, train, airplane, or other vehicle, and configured so that the sensor(s) are able to take arterial measurements of a subject. As another example, a measuring device may be incorporated into smart furniture and configured so that the sensor(s) is in direct contact with a subject or in close proximity with the subject. As a further example, a measuring device may be incorporated into athletic equipment, such as helmets, racket handles, wrist or headbands, shoes, socks, handle bars, etc., and configured so that the sensor(s) are able to take arterial measurements of a subject.

As used herein, the expression "non-interfering blood pressure measuring device" refers to a measuring device that does not substantially interfere or perturb an artery being measured or provides a constant level of interference. A non-interfering blood pressure measuring device may be used over a long period (e.g. over 1-24 hours), enabling blood pressure readings to be taken over a longer period than practical with traditional cuff-based measurement techniques. Monitoring blood pressure over a longer period enables observations of changes in blood pressure that occur over time, which may provide important information about the health of the subject.

Various cardiovascular properties (e.g., blood pressure and pulse rate) can be measured or estimated in the limbs of a subject, such as from an arm or finger, by measuring changes in the diameter (referred to as "distension") of peripheral arteries ("arterial distension") using a variety of sensors. Some non-limiting examples of non-interfering blood pressure measuring devices that may be used in various embodiments to measure arterial distension include ultrasound sensors, bioimpedance sensors, and photoplethysmographic sensors. Changes in arterial distension (i.e., pulse amplitude) and the mean value of an arterial distension signal received from a peripheral artery sensor may result from variations attributed to changes of the artery, particularly when changing elevations of a limb.

Stress-strain properties of arterial walls may be highly non-linear. At low pressures, an arterial vessel is very elastic, dominated by elastin fibers. At higher pressures, an arterial vessel appears stiffer, dominated by collagen fibers. A very coarse classification of arteries is muscular or elastic, although most arteries may be a combination of muscular and elastic properties. The larger arteries in the central system are predominantly elastic, whereas the arteries in the peripheral system are predominantly muscular. The peripheral arteries are generally thinner and stiffer than the arteries in the central system and the elastic properties are more dependent on the smooth muscles than in the central arteries. The smooth muscles in peripheral arteries are arranged in a spiral pattern, and the arterial expansion with an increase in pressure is predominantly in the radial direction and negligible in the longitudinal direction. Artery walls are in general much stiffer than the surrounding tissues. As a result, the pressure right outside an artery is essentially the same as the pressure outside the limb if no external pressure is applied.

The elastic properties of an artery may vary over time, particularly since the tension in the muscles in the artery typically changes over time according to the state of the person. Further, a number of substances may affect the tension of the muscles in an artery. For example, nitroglycerine relaxes smooth muscles, which generally decreases their stiffness and may cause arteries to expand in diameter even when pressure in the artery remains constant or decreases.

Some contemporary blood pressure measuring devices measure the distension of an artery by measuring the expansion or change in diameter of the artery with each heartbeat. Accurately converting the measure of arterial distension into a calibrated blood pressure (e.g., a calibrated diastolic blood pressure value) requires knowledge of certain properties of the artery. In particular, it is usually required to know at least the stiffness or elasticity of the artery in order to convert dimensional characteristics like arterial distension into a measurement of blood pressure. However, estimating and/or determining such arterial properties using conventional techniques is not straightforward. In addition, conventional techniques generally interfere with (i.e., perturb) the artery being measured.

Previous attempts at providing accurate non-interfering blood pressure measuring devices have suffered from calibration problems, particularly for continuous measurements, since arterial properties change so frequently. When the calibration of a non-interfering blood pressure measuring devices is inaccurate, the blood pressure calculated from dimensional characteristics (e.g., cross-sectional area) of an artery will be inaccurate. Some solutions that acknowledge the variation in arterial properties over time suggest recalibration at regular intervals.

Various embodiments include methods, systems, and devices for calibrating a blood pressure measuring device for measurements from an artery in an extremity of a subject without requiring a reference device (e.g., an inflatable cuff). Various embodiment methods may include determining a profile or shape of a pulse waveform representing arterial distension, over the duration of a pulse. The arterial distension pulse shape of each pulse in a series of pulses may be measured at a measurement location on an extremity of the subject such as an arm or finger. Thus, the pulse shape of each pulse may reflect the measured changes in arterial distension as a function of time. By comparing the pulse shape of each pulse in a series of pulses, a transitional pulse in the series of pulses may be identified. The transitional pulse may be identified by a characteristic change in pulse shape, which is believed to be associated with the onset of arterial buckling but not necessarily representing the buckling point. The characteristic change indicating a transitional pulse may be identified in the diastolic tail portion of the pulse shape plotting pressure versus time.

FIG. 1A illustrates a non-interfering blood pressure measuring device 100 configured to determine blood pressure in an artery of a subject 5 in accordance with various embodiments. The non-interfering blood pressure measuring device 100 may include a computing device 230, that may operate as a control unit remote from a skin-contact device 101 using wireless signals 250 to communicate with the skin-contact device 101 for processing data. The computing device 230 may be a smartphone, watch-phone, tablet, laptop, or other type of computer device. The skin-contact device 101 may include a sleeve 150 containing a processor and transceiver for communicating with the computing device 230. Data processing may be performed in the skin-contact device 101 operating as a computing device, the computing device 230, or a combination of both. In addition, the skin-contact device 101 may have a separate power source, such as by a wire coupled to a nearby source of power (e.g., electrical outlet or battery).

In various embodiments, the location of the non-interfering blood pressure measuring device 100, and particularly the skin-contact device 101, the measurement location of the sensors, and the location of the measured artery may be within close proximity of one another. However, the measurement location does not necessarily have to be coincident with the location of the measuring device. For example, various embodiments may include an ultrasound-based sensor that performs the measurement on a particular location at a distance from the ultrasound-based sensor.

Various types of sensors and measuring devices may be used to measure dimensional characteristics of an artery. Some examples of sensors and measuring devices include devices that employ technologies such as ultrasound, nuclear magnetic resonance, propagating electro-magnetic waves, optical sensing, and/or bioelectrical impedance. For example, ultrasound may be used to measure an artery wall or flow velocity (i.e., Doppler velocimetry). Nuclear magnetic resonance may also be used to measure arterial dimensions. Other types of sensors and measuring devices include devices capable of detecting a propagation property of electro-magnetic waves. In addition, optical instruments may be used to detect and measure arterial dimensions (e.g. photoplethysmography) and/or flow velocity. Bioelectrical impedance may be measured, particularly in applications in which arterial dimension and/or flow velocity may be detected from the bioelectrical impedance variations. Additional devices suitable for measuring dimensional characteristics of an artery may be used in accordance with various embodiments.

Figure 1B:
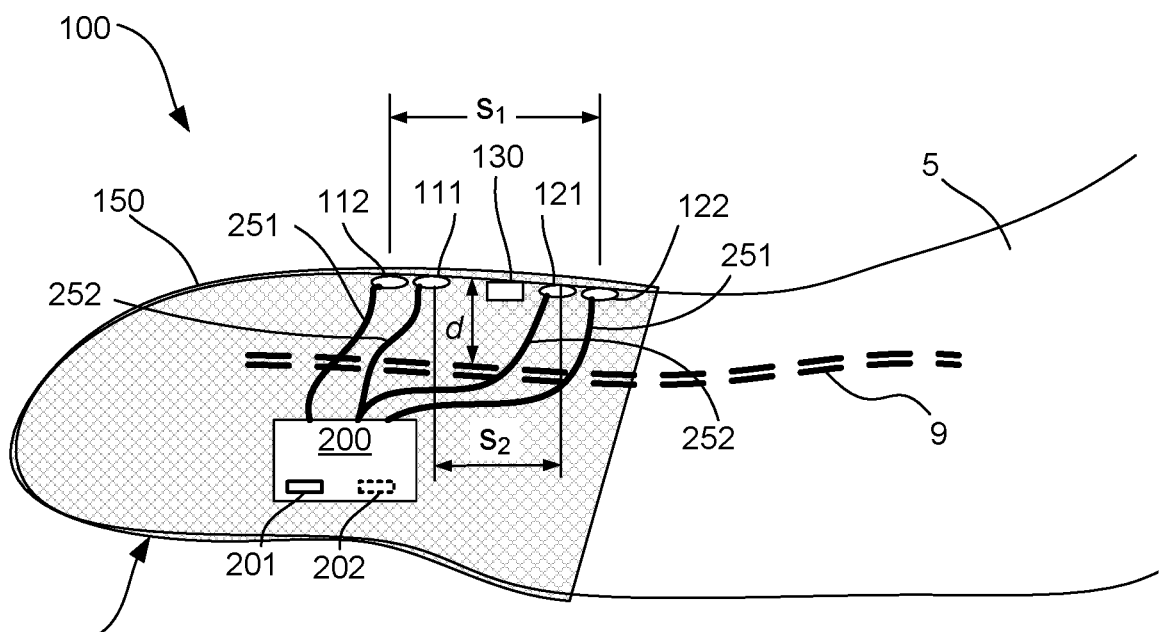
FIG. 1B is a schematic diagram of a non-interfering blood pressure measuring device according to various embodiments.

FIG. 1B illustrates an example of a non-interfering blood pressure measuring device 100 configured to measure blood pressure from an artery 9 in a limb of a subject 5 suitable for use with the various embodiments. As the various embodiments are applicable to a variety of non-interfering blood pressure measuring device, the examples of non-interfering blood pressure measuring device 100 illustrated in FIGS. 1A and 1B are provided merely for identifying examples and representative components that may be involved in implementing various embodiments. Thus, the examples in FIGS. 1A and 1B are not intended to limit the scope of the claims to the illustrated types of non-interfering blood pressure measuring device.

A non-interfering blood pressure measuring device 100 may be placed at a particular location on the subject 5 being measured (i.e., a select portion of the subject's body). For example, the skin-contact device 101 of the non-interfering blood pressure measuring device 100 may include a sleeve 150 formed as a unitary structure that wraps partially or completely around a limb of the subject 5 (e.g., a sleeve on a subject's fingertip or a watch on the subject's wrist). Alternatively, the non-interfering blood pressure measuring device 100 may include sets of individual patches (each including one or more sensors) that are separated from one another. The sleeve 150 may be formed as an elastic band that incorporates a patch or patches with electrodes and a pouch or 'pocket' for holding electronics, such as a control unit 200.

The sleeve 150 may be sized to ensure relatively low levels of counter pressure (i.e., inwardly from a surface of the skin) to ensure the underlying artery is not perturbed. The constant counter pressure may be considered "minor" as long as it is below a diastolic pressure (~90 mmHg) of the subject. The counter pressure may be below 60 mmHg and may preferably be closer to 25 mmHg, which is far more comfortable to the subject. Such a minor constant counter pressure, which may be comparable to the pressure applied by compression stockings, will generally be lower than the pressure applied by an inflatable cuff-type blood pressure device (~200 mmHg). In addition, the application of the minor constant counter pressure may stabilize the veins without hampering a return blood flow. As a result of the minor constant counter pressure, a measurement signal may become larger because of slight modifications to the stress-strain relationship.

The non-interfering blood pressure measuring device 100 may include multiple sensors, such as sets of electrodes 111, 112, 121, 122 and one or more elevation sensors 130. The sets of electrodes 111, 112, 121, 122 may be integrated into the inside surface of the sleeve 150 (i.e., configured to face the subject's skin when worn thereon) that presses against the skin. A firm and even engagement between the skin and the sensor may be desirable.

The sets of electrodes 111, 112, 121, 122 may be used for measuring one or more parameters using bioelectric impedance, and the control unit 200 coupled to the electrodes for processing data. A first set of electrodes may include a first inner detection electrode 111 and a first outer excitation electrode 112. A second set of electrodes may include a second inner detection electrode 121 and a second outer excitation electrode 122. Alternatively, a single electrode may function as both the excitation and measurement electrode such that only one set of two electrodes may be included. In addition, more than four electrodes 111, 112, 121, 122 may be included.

The electrodes 111, 112, 121, 122 may be positioned on a portion of skin of the limb of the subject 5. The second set of two outer excitation electrodes 112, 122 may be placed with an outer separation distance $S_1$ between the electrodes somewhat larger than the depth d at which the artery 9 is embedded in the limb. At the measurement area, a depth d may be less than 0.5 cm, but the separation may be considerably larger, only confined by the length of the limb. The first set of two inner detection electrodes 111, 121 may be placed with an inner separation distance $S_2$, which is less than the outer separation distance $S_1$ and disposed between the two outer excitation electrodes 112, 122. The inner separation distance $S_2$ may be approximately equal to the depth d of the artery or greater. At the measurement area, the inner separation distance $S_2$ may be from 1-2 mm to several centimeters. For example, the inner separation distance $S_2$ may be approximately 0.75 cm and the outer separation distance $S_1$ may be approximately 1.5 cm.

In the various embodiments, an elevation sensor 130 may provide an output that may be continuously converted to a measure of the elevation of the measuring location. For example, an instantaneous elevation or change in elevation may be obtained by double integration of an acceleration signal, such as provided by an accelerometer on the non-interfering blood pressure measuring device 100 or placed at the measuring location. The estimation of elevation or change in elevation of the measuring area may be validated by a level signal provided by an angular sensor mounted on the non-interfering blood pressure measuring device 100 or at the measurement location. A horizontal level may imply a higher likelihood for a position of the measuring site around the middle of the dynamic range for the elevation based on the range of movement of the limb on which the non-interfering blood pressure measuring device 100 is positioned. Similarly, a vertical position may imply a high likelihood for being at one of the extremes of the elevation of the limb on which the non-interfering blood pressure measuring device 100 is positioned.

In various embodiments, variations of the hydrostatic pressure may be continuously evaluated based on outputs from the elevation sensor 130. For example, an elevation difference of 60 cm will correspond to a 47 mmHg arterial pressure change, while a mean arterial pressure at heart level may be around 100 mmHg. Thus, changes in elevation estimated based on a 3D accelerometer with measurements integrated to detect position changes, may be combined with information from a high resolution barometer in order to better determine the elevation of the measuring location.

In various embodiments, the non-interfering blood pressure measuring device 100 may include a control unit 200, which may register and/or process outputs from the electrodes 111, 112, 121, 122 and/or the elevation sensor 130. Values from sensor measurements may be stored in optionally provided memory 202. Alternatively, external memory may be operatively coupled to the processor 201, directly or indirectly through the control unit 200. The control unit 200 may regulate and/or control the timing and/or output levels of the electrodes 111, 112, 121, 122. The control unit 200 may include one or more processors 201 configured to make intermediate and/or final calculations and determinations regarding blood pressure measurements. For ease of description and illustration, some detailed aspects of the control unit 200 are omitted. However, the control unit 200 may include some or all of the further detailed aspects described with respect to the computing device 230 in FIG. 1A.

While the control unit 200 is illustrated as a single unit, multiple control units may be provided. For example, a computing device (e.g., 230 in FIG. 1A) remote from the skin-contact device 101 may be an additional control unit. Alternatively, more than one control unit may be included within or on the skin-contact device 101. The multiple control units may operate together, sharing responsibilities; one control unit may act as a master over one or more other control units; or a combination thereof. Alternatively, the computing device remote from the skin-contact device 101 may operate exclusively as the control unit. Although connections 251, 252 are illustrated as wired connections, the control unit 200 may include one or more wireless connections, such as using one or more wireless transceivers and antennas.

Figure 2:
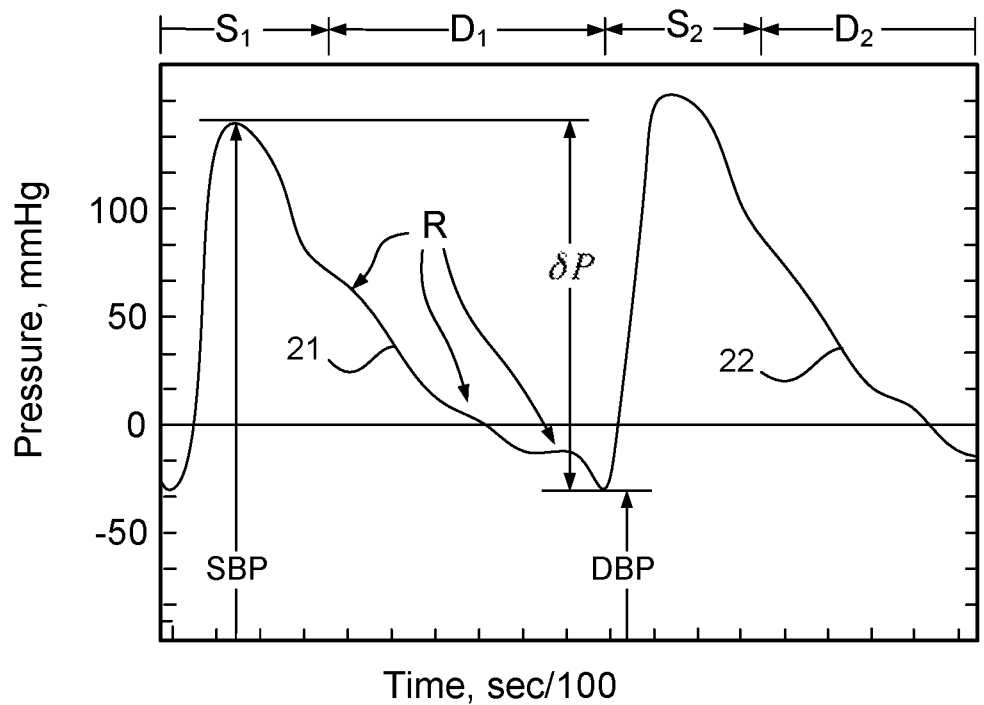
FIG. 2 is a graph of pressure versus time for a series of pulses, noting particular elements according to various embodiments.

FIG. 2 is a graph of blood pressure during a first pulse 21 and a substantial portion of a second pulse 22 showing variations in pressure (i.e., the vertical axis, measured in mmHg) over time (i.e., the horizontal axis, measured in sec/100) that occur during a pulse. In various embodiments, a non-interfering blood pressure measuring device (e.g., 100) may be used to measure arterial distension for generating the graph in FIG. 2. The maximum pulse pressure achieved in a pulse is referred to as the systolic blood pressure (SBP), the minimum pulse pressure is referred to as the diastolic blood pressure (DBP), and a difference between the two is referred to as the pulse pressure δP. Each of the first pulse 21 and the second pulse 22 are general representations of pulse waveforms of pulse pressures that occur after each contraction of the left heart ventricle.

A pulse is considered as having three parts. A first part $S_1$, $S_2$ referred to as the systolic phase, reflects the immediate rise of the pressure as a consequence of the ejection from the heart. A third part includes reflections R, which form oscillations occurring during the diastolic phase that result from discontinuities in the arterial system, such as bifurcations or diameter changes. The reflections R may vary among subjects and tend to be more pronounced in younger subjects and virtually non-existent in older subjects. A second part $D_1$, $D_2$ referred to as the diastolic phase, reflects the fall in pressure after the systolic phase. Various embodiments determine the calibrated diastolic blood pressure by recognizing a characteristic change of the diastolic part of the pulse waveform that occurs when the transmural pressure approaches zero.

While FIG. 2 shows pressure as the vertical axis, similar pulse shapes are expected to be observed using various measurements of physiological properties related to blood pressure. For example, if arterial distension is plotted against time, a similar pulse shape may be expected, since incremental blood pressure variations and distension variations are generally proportional. Thus, measurements taken at a measurement location need not be converted into blood pressure as part of the various embodiment methods of calibrating a non-interfering blood pressure measuring device.

The diastolic phase is generally characterized by an exponentially decaying pressure. The exponential decay asymptotically approaches a value typically higher than the venous pressure, but is redirected before doing so upon the occurrence of the second pulse 22 (i.e., a subsequent pulse), which starts the systolic phase $S_2$ of the second pulse 22. The exponential decay may be caused by the arterial system being connected with the veins through the capillary network with a high fluid-flow resistivity and the veins being much more elastic than the arteries. Thus, the venous system essentially behaves like a capacitor, which has a capacitance much larger than that of the arterial system. Propagation effects may play an insignificant role for the decay since a time-constant of the decay may be much larger than the pulse propagation time through the arterial system.

Various embodiments correlate conditions under which the transmural pressure reaches zero with observable changes that occur in the later part of the diastolic phase of the pulse shape (i.e., the pulse tail). The pulse pressure generated by the heart of the subject may be generally constant on short time scales, such as under a minute. However, external pressures applied to a measurement location, such as a limb of a subject, may be changed quickly to affect a transmural pressure locally in an artery at the measurement location. Thus by applying a combination of hydrostatic pressure and a counter pressure to the measurement location equal to a diastolic blood pressure over a short time scale, the transmural pressure will approach or reach zero, which may be reflected in changes to the diastolic phase of measured pulses.

Figure 3:
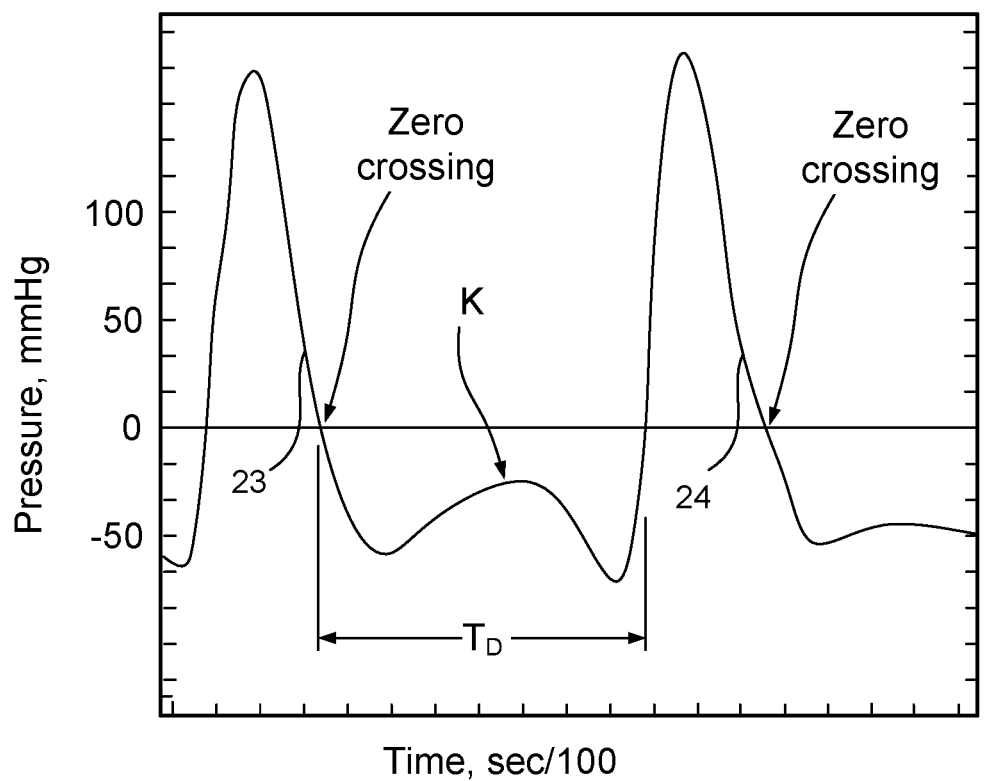
FIG. 3 is a graph of pressure versus time for a series of pulses including a transitional pulse, noting particular elements according to various embodiments.

FIG. 3 is a graph of a third pulse 23 and a portion of a fourth pulse 24 showing variations in pulse pressure (i.e., the vertical axis, measured in mmHg) over time (i.e., the horizontal axis, measured in sec/100). In various embodiments, a non-interfering blood pressure measuring device (e.g., 100) may be used to measure arterial distension for generating the graph in FIG. 3. The third pulse 23 and fourth pulse 24 represent transitional pulses that where achieved by applying a constant counter pressure of 40 mmHg to the subject with a wrist-worn measuring device sleeve and decreasing the internal pressure by increasing the hydrostatic pressure obtained by elevating the measurement location (e.g., by raising the subject's arm).

The third pulse 23 includes a kink K in a lowest segment of the diastolic tail, which forms at an elevation or inclination higher than the level of the subject's heart. Various embodiments associate the kink K with the transmural pressure reaching zero, at least for the diastolic part of a pulse. The kink K may correspond to an onset of arterial buckling but does not necessarily represent the buckling point of the artery. Although smaller or less significant bends may be observed without the constant counter pressure, the formation of the kink may be more pronounced when a minor counter pressure around the measuring device and the limb is applied. The transition from the shapes illustrated in FIG. 2 to the shape illustrated in FIG. 3 may occur after only a very small increase in elevation of the measurement location when the combined effect of a counter pressure and hydrostatic pressure causes the transmural pressure to approach zero.

The kink K corresponds to an additional concave curve or bend at the end of the diastolic part of the pulse waveform. As the size and shape of the kink K may vary, a threshold deviation from a predetermined pulse shape may be used to recognize a kink K that may be properly associated with the transmural pressure reaching zero in the diastolic tail. The predetermined pulse shape may help distinguish signs of the transmural pressure reaching zero from other minor oscillations that may occur. For example, the threshold deviation may include a designated deviation percentage from the predetermined pulse shape. Thus, deviations in a diastolic tail of a measured pulse waveform that meet (or exceed) the designated deviation percentage may be used to identify a pulse in a series of blood pressure pulses as being a transitional pulse. The predetermined pulse shape may be based on a designated waveform (e.g., a mean pulse waveform). Alternatively, rather than a designated deviation percentage, the threshold deviation may be a designated peek pressure value in the diastolic tail, which if met or exceeded may be used to identify the transitional pulse. As a further alternative, the threshold deviation may include a designated rate of change, which if met or exceeded may be used to identify the transitional pulse.

While FIG. 3 shows pressure on the vertical axis, similar pulse shapes are expected to be observed using various measurements of arterial properties related to blood pressure. For example, if arterial distension is plotted against time, a similar pulse shape may be expected when the measurement location is at the same elevation as the subject's heart. Thus, measurements taken at a measurement location need not be converted into blood pressure to observe the changes in pulse shape used in the various embodiment methods of calibrating a non-interfering blood pressure measuring device.

Various embodiments use a combination of a constant minor counter pressure and/or changing hydrostatic pressure as known applied pressures, since such small pressures do not tend to perturb arterial measurements and may be readily known or calculated.

Figure 4A:
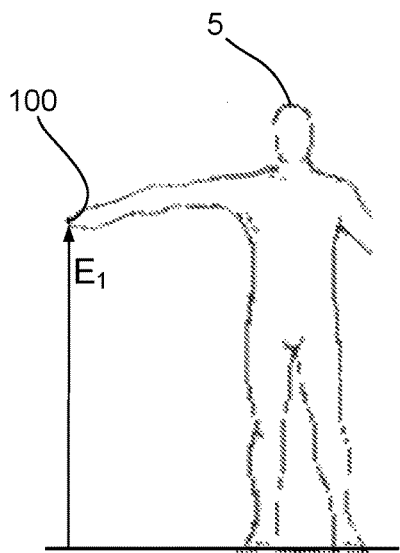
FIG. 4A illustrates a front elevation view of a subject wearing a measuring device on a wrist held in a lowered position according to various embodiments.
Figure 4B:
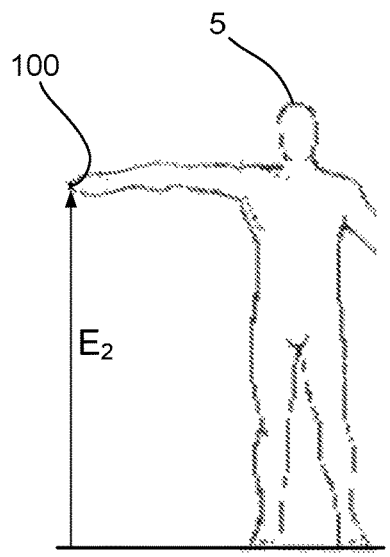
FIG. 4B illustrates a front elevation view of the subject of FIG. 4A with the wrist held at heart level according to various embodiments.
Figure 4C:
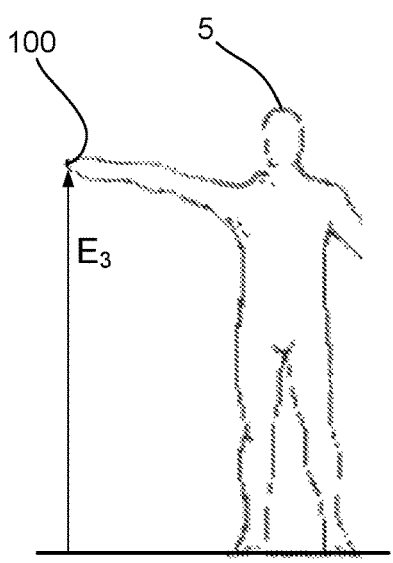
FIG. 4C illustrates a front elevation view of the subject of FIG. 4A with the wrist held above heart level according to various embodiments.

FIGS. 4A-4C illustrate a subject 5 holding out a limb in three different positions. The subject 5 is wearing a non-interfering blood pressure measuring device 100 in the same location in all three positions. Alternatively, a different non-interfering blood pressure measuring device may be used in place of the non-interfering blood pressure measuring device 100.

In various embodiments, the non-interfering blood pressure measuring device 100 may initiate continuous pulse pressure measurements in an initial position below the subject's heart level, such as shown in FIG. 4A. The non-interfering blood pressure measuring device 100 may measure and/or record arterial distension signals. In addition, the arterial distension signals may be filtered with a high-pass filter, such as by filtering measured values slightly below the reciprocal pulse rate (e.g., 10% to 50% below the reciprocal pulse rate).

The non-interfering blood pressure measuring device 100 may include a counter pressure device, such as one or more of a patch, band, sleeve, or cuff that may provide a constant minor counter pressure (e.g., 10-60 mmHg), such as on the subject's finger, wrist, or arm. The non-interfering blood pressure measuring device 100 does not need to be an inflatable device since minor levels of pressure may be applied to the tissue surrounding the artery being measured by patches, bands, and/or sleeves as well. In this initial position, the non-interfering blood pressure measuring device 100 is disposed at a first elevation $E_1$. Measurements may be displayed directly on the non-interfering blood pressure measuring device 100 or output by the non-interfering blood pressure measuring device 100 for display and/or analysis by a remote computing device. Once the measurements demonstrate a constant pulse rate, the subject 5 may be instructed to raise his or her limb (i.e., active movement by the subject 5) or the subject's limb may be moved for them by an assistant or other apparatus (i.e., passive movement by the subject 5).

In FIG. 4B, the subject's limb has been raised to slightly above the subject's heart level, positioning the non-interfering blood pressure measuring device 100 at a second elevation $E_2$. The change in elevation between the first elevation $E_1$ and the second elevation $E_2$ causes a change in hydrostatic pressure within the artery at the measurement location, which when combined with the minor counter pressure may equal a diastolic blood pressure of the subject 5. In some embodiments, is it preferable to compensate for the distance between heart level and shoulder at which the main artery enters the peripheral arm. Typically 5-20 cm may be subtracted from the elevation height to compensate for this distance. Alternatively, compensation for this distance need not be included. This may mean the transmural pressure is at or near zero, which may cause a significant change of the tail end of the diastolic part of the pulse shape waveform. Such a change may be identified by a processor in the non-interfering blood pressure measuring device 100 or a remote processor connected thereto. If the second elevation $E_2$ is the earliest point from the first elevation $E_1$ when a transitional pulse is identified (i.e., a pulse including the signature kink K in the tail of the diastolic part), the second elevation $E_2$ may be used by a processor to calculate the corresponding hydrostatic pressure, and thus determine an calibrated diastolic blood pressure for calibrating the blood pressure measuring device in accordance with various embodiments. Thus, the transitional pulse may be associated with the hydrostatic pressure at the first upward level, relative to the heart, at which a significant change in shape is identified in the diastolic part of a pulse. In some embodiments, the measurements may not start until the second elevation $E_2$ shown in FIG. 4B.

In FIG. 4C, the subject's limb has been raised to a third elevation $E_3$, above the second elevation $E_2$. The change in elevation between the second elevation $E_2$ and the third elevation $E_3$ will cause additional changes in hydrostatic pressure and may continue to measure an irregular pulse shape waveform. Such indications may further corroborate an earlier determination about the second elevation $E_2$ being properly associated with the transitional pulse used to determine the calibrated diastolic blood pressure. For example, if the kink becomes more pronounced at an elevation higher than the second elevation $E_2$ (e.g., $E_3$), instructions may be given to lower the subject's limb slowly to confirm the determined calibrated diastolic blood pressure from the second elevation $E_2$.

The effect of a change in hydrostatic pressure may be readily determined from the change in elevation of a measurement location. When the elevation of the measurement location changes by a known distance, the hydrostatic pressure will change from a previous value at the measurement location. Various embodiments assume that if the pulse rate is constant, the blood pressure will also remain constant, which implies that any change in blood pressure at the measuring site as a result of a height change may be primarily associated with the hydrostatic pressure change. Thus, an adjustment for the change in hydrostatic pressure may be incorporated into an expression of the average of the mean arterial pressures as follows:

$$\langle P_i \rangle = \langle P_{i-1} \rangle + \Delta P_H = \langle P_{i-1} \rangle + \rho g \Delta h \quad (1),$$

where $\Delta P_H$ is the hydrostatic pressure change, $\rho$ is a density of the fluid (i.e., the blood density), g is the gravitational acceleration (i.e., 9.8 m/s²), and $\Delta h$ is a distance corresponding to the change in elevation (i.e., a height change).

Various embodiments identify a transitional pulse used to determine a calibrated diastolic blood pressure by recognizing a characteristic change in shape of the diastolic tail of a pressure pulse waveform (i.e., the "pulse shape"). The characteristic change in pulse shape may be identified by various methods.

Generally, the minimum pressure value of a pulse occurs very close to the onset of a subsequent pulse. A strong indication that zero transmural pressure conditions have been achieved or are nearly achieved in the last part of a pulse is when a minimum pressure value or near minimum pressure value does not occur at the end of the pulse (i.e., the beginning of the subsequent pulse). Thus, the characteristic change in pulse shape may be identified by recognising a pulse within the series of pulses that includes a minimum or near minimum pressure value occurring at a predetermined time earlier than expected, following a first zero crossing of the pulse shape, as illustrated in FIG. 3. For example the predetermined time may be a fraction (e.g., ½, ⅓, or ⅔) of a diastolic tail period $T_D$. The diastolic tail period $T_D$ may be defined as the period from the first zero crossing with a negative gradient of the pulse shape after the systolic peak to the next consecutive zero crossing of the pulse shape having a positive gradient. In addition, the minimum pressure value occurring at the predetermined time may need to also have a corresponding amplitude that is a predetermined fraction (e.g., ¼ to ½) of the maximum pulse amplitude for the pulse in question.

In various embodiments, the characteristic change in pulse shape may additionally or alternatively be characterized by cross-correlating identified kinks at more than one measurement elevation. This technique compares individual the pulse shapes of pulses in a series of pulses during the period in which the changing external pressure is applied. For example, a predetermined percentage (e.g., 20%) deviation in measurements occurring during the diastolic tail period $T_D$ may be attributed to the characteristic change in pulse shape of a transitional pulse. In this way, the characteristic change in pulse shape may be recognized by comparing individual pulses in the series of pulses and identified a pulse within the series of pulses that deviates from a mean pulse shape within the series of pulses by a predetermined percentage.

In various embodiments, the characteristic change in pulse shape may additionally or alternatively be identified by calculating an expected pulse shape for at least the diastolic tail period $T_D$ and comparing measured values of the diastolic tail period in each pulse shape to the expected pulse shape. For example, measured values may be fitted to an exponential decay of the diastole and pulses with significant deviations there from may be identified as a transitional pulse or at least a transitional pulse candidate.

Additionally or alternatively in various embodiments, the characteristic change in pulse shape may be identified by changes in the reflections (e.g., R). Over short periods, the reflection sites tend to remain constant. Thus, deviations from expected reflections may indicate a characteristic change in pulse shape associated with the transmural pressure approaching zero. For example, a lack of reflections or reduction in size of reflections in a pulse waveform may be considered the characteristic change in pulse shape associated with the transmural pressure approaching zero.

Figure 5:
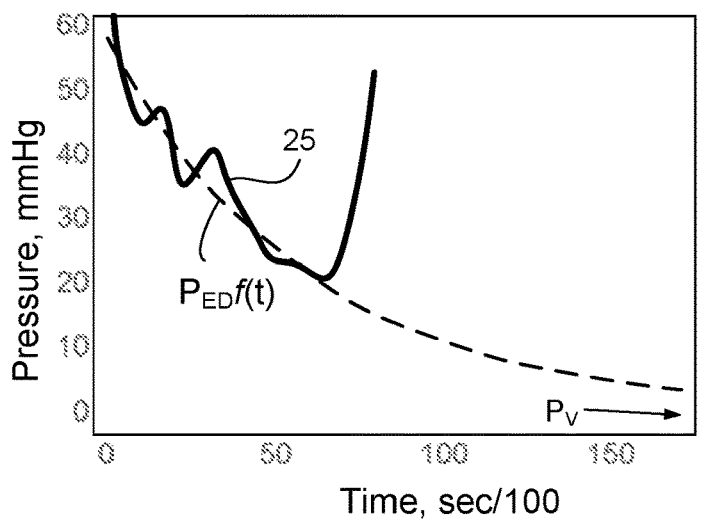
FIG. 5 is a graph of pressure versus time for a pulse pressure of a diastolic phase of an initial pulse and the start of a subsequent pulse, along with a curve matching an exponential decay of the diastolic phase according to various embodiments.

FIG. 5 is a graph of another pulse shape 25 showing changes in pressure (i.e., the vertical axis, measured in mmHg) over time (i.e., the horizontal axis, measured in sec/100) during a diastolic phase and part of a subsequent systolic phase. In various embodiments, a non-interfering blood pressure measuring device (e.g., 100) may be used to measure arterial distension for generating the graph in FIG. 5. Superimposed on the pulse 25 is a decaying exponential function $P_{ED}f(t)$, expressing the exponential decay of the pulse 25 during and extended well beyond the diastolic phase. An extrapolation of exponentially decaying pressures $P_{ED}$ (i.e., the pressures during the diastolic portion of the pulse pressure) over time may be express as:

$$P_{ED} = a \, \exp\!\left(-\frac{t}{t_0}\right) + b, \quad (2)$$

where a represents an arterial distension amplitude of the diastolic phase, t represents a length of time, and $t_0$ represents a time-constant of the decay. The time-constant of the decay $t_0$ may reflect the resistance of the capillary network connecting an artery to veins in conjunction with the capacity of the veins. Equation (2) also includes an asymptotic value b that represents the underlying vein pressure contributions.

Various embodiments determine estimated values of exponentially decaying pressures $P_{ED}$ using an incremental sensitivity k applied to measured values corresponding to the diastolic phase of a pulse. In this regard, consideration need not be given to estimated pulse pressures not corresponding to the diastolic phase (e.g., the systolic phase). A plot of the estimated exponentially decaying pressures $P_{ED}$ following the peak pressure of a pulse may be used to determine a coefficient that fits the exponential decay function of equation (2) to the estimated exponentially decaying pressures $P_{ED}$. Assuming the arterial distension amplitude a may be determined along with the incremental sensitivity k, and considering that the venous pressure may be low, the determined coefficient may be an additive (or subtractive) value that represents the asymptotic value b in equation (2). The determined coefficient may be different from the venous pressure, due to biases inherent in most measuring schemes, many of which may be relatively large. Nonetheless, a value of the underlying venous pressure may be used in determining the coefficient by subtracting that value from the asymptotic value b determined from the curve fitting. Thus, the determined asymptotic value b minus the venous pressure may equal the coefficient applied to the otherwise estimated values of pulse pressure to determine a calibrated blood pressure.

Various embodiments fit the exponentially decaying function $P_{ED}f(t)$ to the pulse pressure estimates (or raw measurement data, such as arterial distension) during diastolic phases. The curve fitting procedure may be a least-squares procedure, may be based on fitting a straight line to the logarithm of the data values with the expected asymptotic value added, or may be another well known curve-fitting method. The diastole may be defined as starting at the time instance after the first dip of the pulse in which the second derivative of the measured pulse waveform with respect to time is positive and ending at the onset of the subsequent pulse.

Figure 6A:
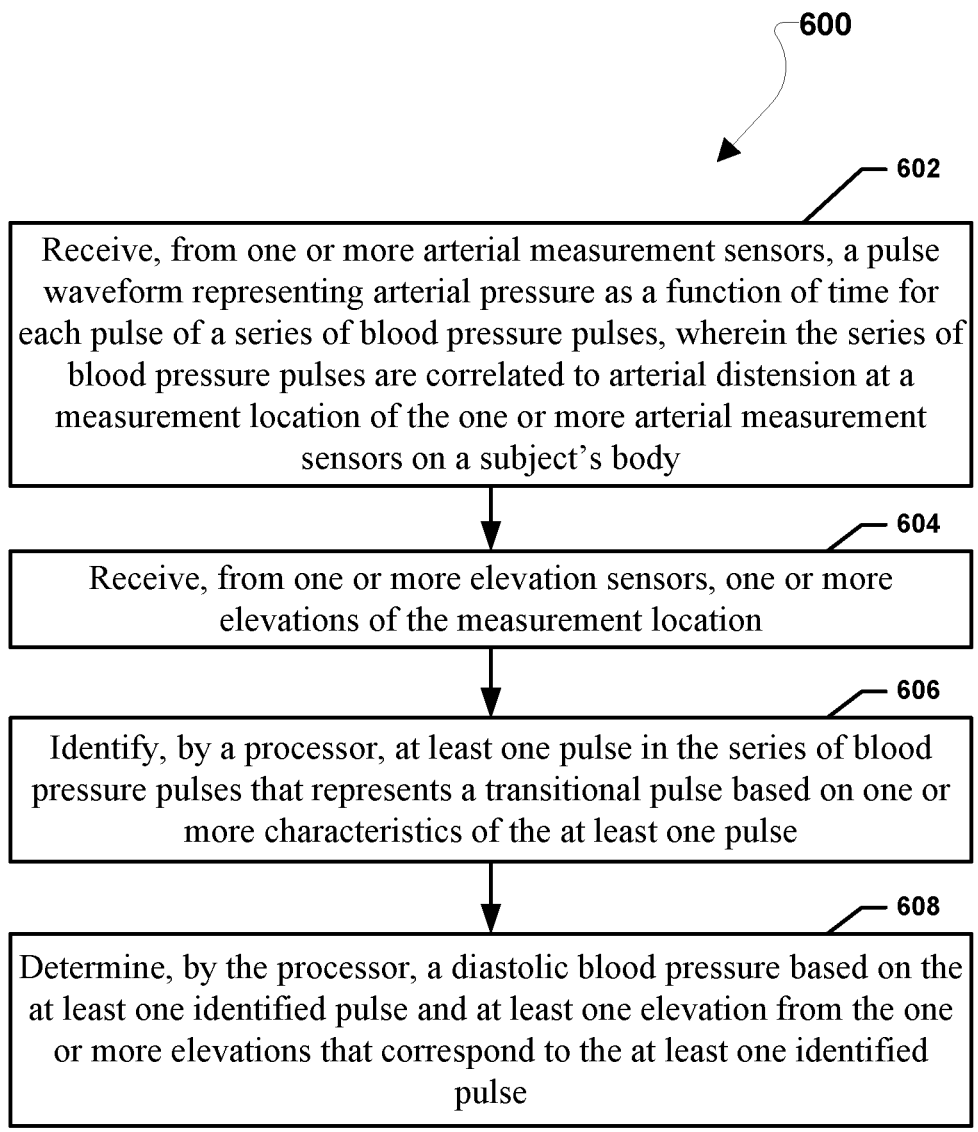
FIG. 6A is a process flow diagram illustrating an embodiment method of calibrating a blood pressure measuring device according to various embodiments.

FIG. 6A illustrates a method 600 of measuring a blood pressure measuring device. The blood pressure measuring device may be configured to take measurements on an artery in a limb of a subject according to various embodiments. The various operations of the method 600 may be performed by a blood pressure measuring device (see e.g., FIG. 1), including one or more sensor(s) and a control unit or other computing device and/or processor in communication with a blood pressure measuring device.

In block 602, a processor may receive, from one or more arterial measurement sensors, a pulse waveform representing arterial pressure as a function of time for each pulse of a series of blood pressure pulses. The series of blood pressure pulses may be correlated to arterial distension at a measurement location of the one or more arterial measurement sensors on a subject's body. Arterial pressure measurements associated with blood pressure may be taken from an artery in an extremity (e.g., a finger, wrist, or arm) of a subject. The arterial measurement sensors may be one or more non-interfering blood pressure measurement devices directly or indirectly (e.g., from memory or through another intermediate device). Some non-limiting examples of non-interfering blood pressure measuring devices that may be used with the various embodiments include ultrasound sensors, bioimpedance sensors, and photoplethysmographic sensors. The arterial pressure measurements may represent arterial pressure as a function of time for a series of pulses correlated with arterial distension at a measurement location on a limb of a subject.

In some embodiments, a minor counter pressure may be applied while the continuous arterial pressure measurements are taken. Applying a small amount of counter pressure may help stabilize the arterial pressure measurements. The processor may filter the received measurement signals in various ways and at various stages of the operations of method 600. The filtering may initially be a high-pass filtering to eliminate low-frequency fluctuations caused by unwanted perturbation. Alternatively or additionally, wavelet filtering may be performed in relation to pulse localization in time, amplitude and shape, and periodicity.

In addition, the processor may store the measurements. In various embodiments, the pulse shapes may be recorded continuously as the sensor data is received, and the pulse rate may be measured and averaged over a sliding measurement time window. The time window for averaging measurements may be between approximately thirty seconds in duration and approximately two minutes in duration. For example, the processor may store the measured pulses in a memory, such as a database of measured pulses for different observation times.

In block 604, the processor may receive, from one or more elevation sensors, one or more elevations of the measurement location. The elevations may reflect the elevation measurements of the measurement location and correspond to respective ones of the series of pulses. In some embodiments, the one or more elevations may be elevation measurements of the measurement location that the processor can use to calculate the elevation of the measurement site, and thus estimate the hydrostatic pressure in the artery. Thus, during the series of pulses, the limb may be raised from below a heart of the subject to an elevation level with the subject's heart. The limb may continue to be raised beyond the elevation level with the subject's heart. A minor constant counter pressure may be applied on or near the measurement location during the elevation changes.

In block 606, the processor may identify at least one pulse in the series of blood pressure pulses that represents a transitional pulse based on one or more characteristics of the at least one pulse. The one or more characteristics may include amplitude, pulse shape, or any combination thereof. The transitional pulse may be identified by a characteristic change in the pulse shape, particularly of the diastolic tail of the pulse shape. The characteristic change is believed to be generally associated with or caused by the onset of arterial buckling.

In block 608, the processor may determine a diastolic blood pressure based on the at least one identified pulse and at least one elevation from the one or more elevations that correspond to the at least one identified pulse. The diastolic blood pressure determined in block 608 may be used to calibrate the non-invasive blood pressure measuring device. Such calibration may involve correlating the measurement values received from the particular measurement sensor (e.g., ultrasound, bioimpedance, optical, etc.) to the determined calibrated diastolic blood pressure. Such correlation may involve calculating a conversion factor for determining blood pressure based upon sensor measurements. Such a calibration or conversion factor may be stored in memory for use by the non-invasive blood pressure measuring device.

Figure 6B:
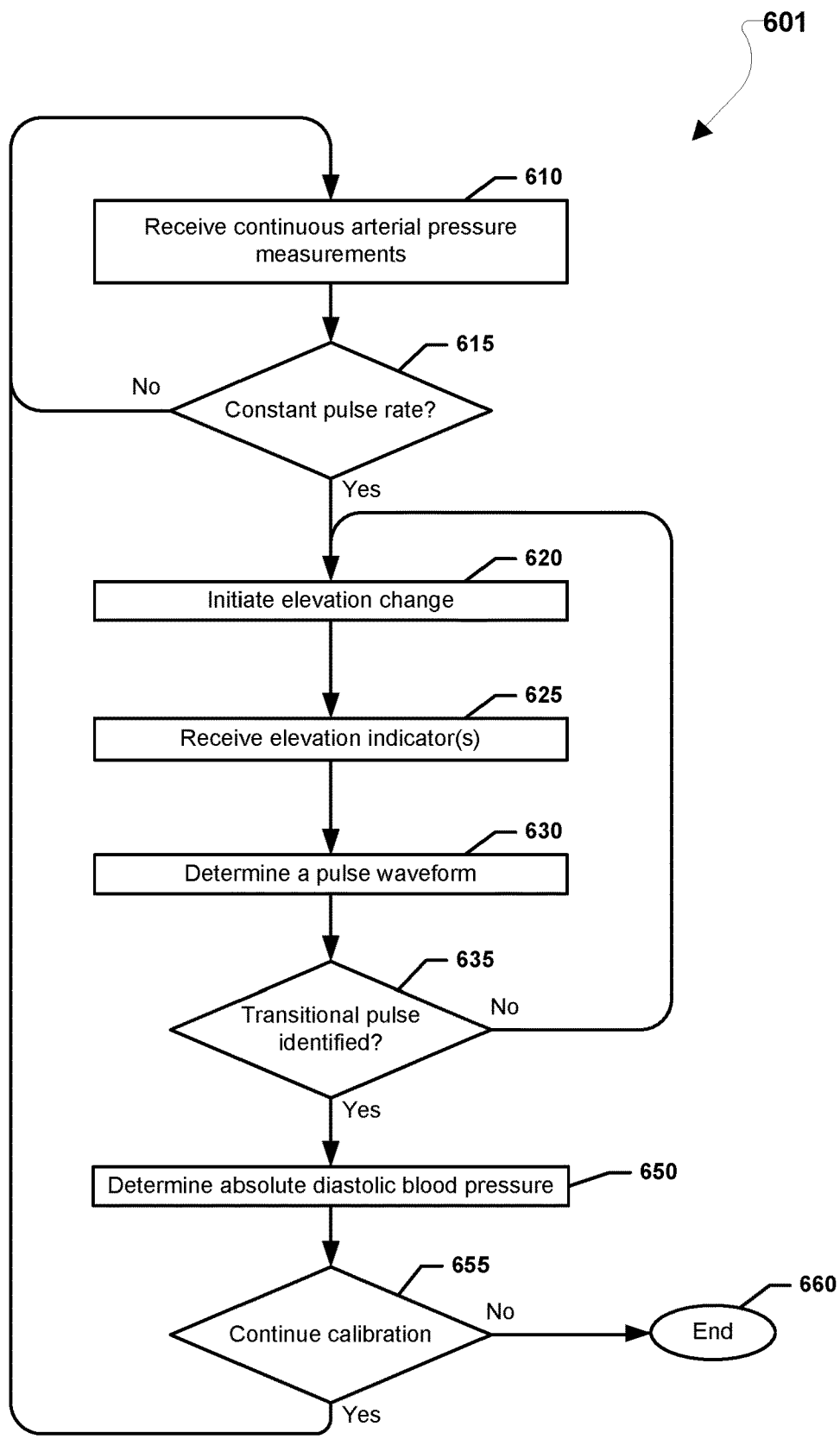
FIG. 6B is a process flow diagram illustrating an embodiment method of calibrating a blood pressure measuring device according to various embodiments.
Figure 7:
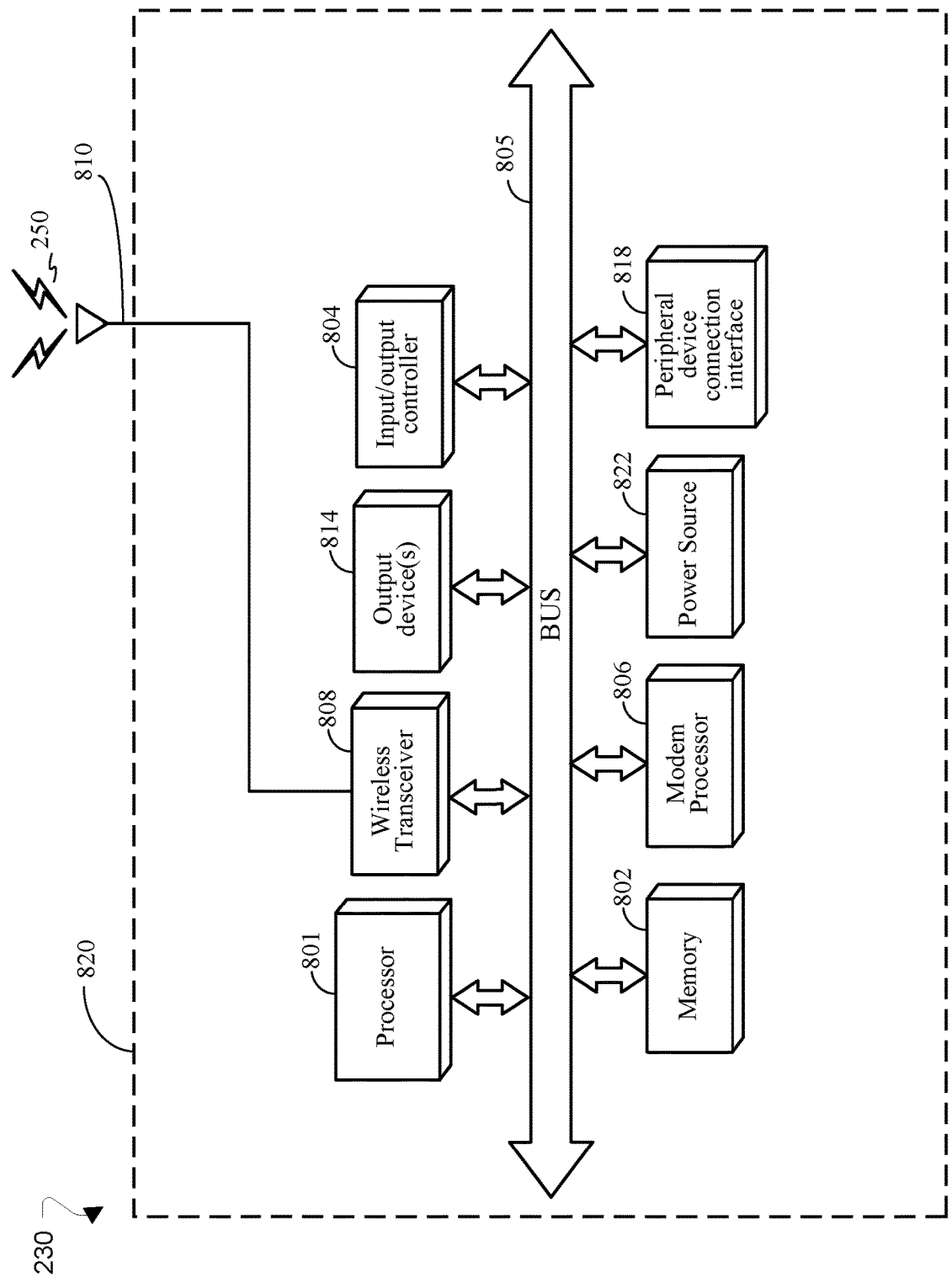
FIG. 7 is a component block diagram of a computing device according to various embodiments.

FIG. 6B illustrates a method 601 of calibrating a blood pressure measuring device according to various embodiments. The blood pressure measuring device may be configured to take measurements on an artery in a limb of a subject. The various operations of the method 601 may be performed by a blood pressure measuring device (see e.g., FIG. 1), including one or more sensor(s) and a control unit or other computing device and/or processor in communication with a blood pressure measuring device.

In block 610, a processor may initiate and receive continuous arterial pressure measurements associated with blood pressure that are taken from an artery in an extremity (e.g., a finger, wrist, or arm) of a subject. The measurements may be received from a non-interfering blood pressure measurement device directly or indirectly (e.g., from memory or through another intermediate device). Some non-limiting examples of non-interfering blood pressure measuring devices that may be used with the various embodiments include ultrasound sensors, bioimpedance sensors, photoplethysmographic sensors or any combination thereof. The arterial pressure measurements may represent arterial pressure as a function of time for a series of pulses correlated with arterial distension at a measurement location on a limb of a subject. In some embodiments, a minor counter pressure may be applied while the continuous arterial pressure measurements are taken. Applying a small amount of counter pressure may help stabilize the arterial pressure measurements. The processor may filter the received measurement signals in various ways and at various stages of the operations of method 601. The filtering may initially be a high-pass filtering to eliminate low-frequency fluctuations caused by unwanted perturbations. Alternatively or additionally, wavelet filtering may be performed in relation to pulse localization in time, amplitude and shape, and periodicity.

In addition, the processor may store the measurements. In various embodiments, the pulse shapes may be recorded continuously as the sensor data is received, and the pulse rate may be measured and averaged over a sliding measurement time window. The time window for averaging measurements may be between approximately thirty seconds in duration and approximately two minutes in duration. For example, the processor may store the measured pulses in a memory, such as a database of measured pulses for different observation times.

In determination block 615, the processor may determine whether the received continuous pulse pressure measurements reflect a constant pulse rate. Ensuring the subject has a constant pulse rate before further analysis may ensure a more accurate calibration of blood pressure measurements.

In response to the processor determining the received continuous pulse pressure measurements do not reflect a constant pulse rate (i.e., determination block 615="No"), the processor may continue to receive continuous pulse pressure measurements in block 610.

In response to the processor determining the received continuous pulse pressure measurements reflect a constant pulse rate (i.e., determination block 615="Yes"), the processor may initiate an elevation change of the measurement location in block 620. Changes to the elevation of the limb on which measurements are being taken, changes the hydrostatic pressure at the measurement location. In some embodiments, initiating the elevation change may include generating an output that indicates the subject should raise or lower the limb on which the measuring device is positioned. The processor may activate a signal that prompts the subject to raise the limb from a lowered position. Alternatively, an assistant, medical practitioner, or person may raise the limb. In some embodiments, the processor may activate an apparatus that physically raises the limb from the lowered position.

In block 625, the processor may receive a series of elevation indicators reflecting the elevation measurements of the measurement location and corresponding to respective ones of the series of pulses. In some embodiments, the series of elevation indicators may be elevation measurements of the measurement location that the processor can use to calculate the elevation of the measurement site, and thus estimate the hydrostatic pressure in the artery. Thus, during the series of pulses, the limb may be raised from below a heart of the subject to an elevation level with the subject's heart. The limb may continue to be raised beyond the elevation level with the subject's heart. A minor constant counter pressure may be applied on or near the measurement location during the elevation changes.

In block 630, the processor may determine a pulse waveform representing arterial pressure as a function of time for each pulse of the series of blood pressure pulses correlated to arterial distension at the measurement location on the limb. The determination of the pulse waveform may be a graphical or mathematical representation of the blood pressure or a measured parameter during each pulse. The determination of the pulse waveform of each pulse may enable the processor to identify one pulse in the series of pulses that is a transitional pulse. The transitional pulse may be identified by a characteristic change in the pulse shape, particularly of the diastolic tail of the pulse shape. The characteristic change is believed to be generally associated with or caused by the onset of arterial buckling.

In determination block 635, the processor may determine whether a transitional pulse is identified from among the determined pulse shapes of the series of pulses. The transitional pulse may be identified as one pulse within the series of pulses that exhibits a characteristic change in pulse shape associated with arterial buckling. In particular, the characteristic change may be recognized in the diastolic tail of the one pulse. The characteristic change in pulse shape may be identified by determining a pulse from the series of pulses that includes a minimum pressure value occurring at a predetermined time following a first zero crossing. Also, the amplitude of the pulse from the series of pulses may be a predetermined fraction of the maximum pulse amplitude for the pulse from the series of pulses. In addition or alternatively, the characteristic change in pulse shape may be recognized by comparing the pulse shape of individual pulses in the series of pulses and identifying a pulse within the series of pulses exhibiting a pulse shape that deviates from a mean pulse shape of the series of pulses by a predetermined percentage. The mean pulse shape may be based on the pulse shape of individual pulses in the series of pulses, based on an average pulse shape for the subject, or based on another pulse designated as the average pulse shape. As a further alternative, the characteristic change in pulse shape may be recognized by identifying one or more pulses having an oscillatory pulse shaped diastolic tail that is immediately preceded by an earlier pulse having a near exponential decay shaped diastolic tail. Further still, the characteristic change in pulse shape may be identified at a lowest segment of the pulse shape.

In response to not identifying a transitional pulse (i.e., determination block 635="No"), the processor may further initiate an elevation change in block 620.

In response to the processor identifying a transitional pulse (i.e., determination block 635="Yes"), the processor may determine a calibrated diastolic blood pressure in block 650. The determination of the calibrated diastolic blood pressure may be from an external pressure indicator of the series of external pressures indicators corresponding to a measured diastolic blood pressure of the transitional pulse. The calibrated diastolic blood pressure determined in block 650 may be used to calibrate the non-invasive blood pressure measuring device. Such calibration may involve correlating the measurement values received from the particular measurement sensor (e.g., ultrasound, bioimpedance, optical, etc.) to the determined calibrated diastolic blood pressure. Such correlation may involve calculating a conversion factor for determining blood pressure based upon sensor measurements. Such a calibration or conversion factor may be stored in memory for use by the non-invasive blood pressure measuring device.

In determination block 655, the processor may determine whether blood pressure measurement calibrations should continue. For further or continuous calibration, the processor may determine the measurements and calibration determination should continue. Also, the processor may receive an input indicating the calibration should continue or cease.

In response to the processor determining not to continue calibration (i.e., determination block 655="No"), the processor may end in block 660. In response to the determining that calibration should continue (i.e., determination block 655="Yes"), the processor may continue to receive continuous pulse pressure measurements in block 610.

The parameters used to calculate blood pressure may be received from any of several sensors known in the art for monitoring vascular dynamics. Such sensors may include an IPG (bioimpedance sensing), PPG (optical sensing), ultrasound for arterial distension and/or flow velocity.

The validation methods of various embodiments may be implemented with one of several signal and data processing devices such as a Digital Signal Processing device, a Mixed Signal Processing ASIC, a field programmable gate array (FPGA) or a dedicated implementation based on a combination of analog and/or digital components.

Various embodiments include a non-interfering blood pressure measuring device. As mentioned above, physical characteristics of an artery, such as the cross-sectional area A, may be measured with an arterial measurement sensor. Such measurements may be used to measure changes in arterial properties. Thus, changes in an arterial cross-sectional area over a pulse, which represent distension of the artery, may be quantified by the difference between the maximum and minimum cross-sectional areas over the pulse.

An embodiment blood pressure measuring device may be configured to transmit data to any of a variety of computing devices. For example, FIG. 8 illustrates a computing device 230 suitable for use in various embodiments. The computing device 230 may exchange data to and/or from the blood pressure measuring devices discussed above, such as the skin-contact device 101, and may perform one or more of the operations of the methods 600 and 601 described herein. For example, DBP, δP, SBP, MAP, and/or measured pulses, hydrostatic pressure, and/or elevation may be sent from the blood pressure measuring device to the computing device 230.

The term "computing device" is used herein to refer to any one or all of cellular telephones, smart-phones, web-pads, tablet computers, Internet enabled cellular telephones, wireless local area network (WLAN) enabled electronic devices, laptop computers, dedicated healthcare electronic devices, personal computers, and similar electronic devices equipped with at least a processor and configured to communicate with a blood pressure measuring device described herein, such as a negligible interfering and negligible perception configuration or form blood pressure measuring device (e.g., a wearable patch, bracelet, anklet, watch, etc.).

In various embodiments, the computing device 230 may include a processor 801 coupled, directly and/or indirectly through bus 805, to an input/output device controller 804 and an optional internal memory 802. The processor 801 may be one or more multicore ICs designated for general or specific processing tasks. The optional internal memory 802 may be volatile or non-volatile memory, and may also be secure and/or encrypted memory, or unsecure and/or unencrypted memory, or any combination thereof. The input/output device controller 804 and the processor 801 may also be coupled to a touch screen panel, such as a resistive-sensing touch screen, capacitive-sensing touch screen, infrared sensing touch screen, etc.

The computing device 230 may have one or more radio signal transceivers 808 (e.g., Peanut®, Bluetooth®, Zig-Bee®, Wi-Fi, RF, cellular, near field, or other WLAN) and antennae 810, for sending and receiving, coupled to each other and/or to the processor 801. The radio signal transceivers 808 and antennae 810 may be used with the above-mentioned circuitry to implement the various wireless transmission protocol stacks and interfaces. The computing device 230 may include one or more modem processors 806 coupled to the processor 801. The one or more modem processors 806 may enable communication via a wide area network, local area network, personal area network, near field, etc. The one or more modem processors 806 may also include reception of wireless signals 250 from global navigation satellite systems (GNSS).

The computing device 230 may include a peripheral device connection interface 818 coupled to the processor 801. The peripheral device connection interface 818 may be singularly configured to accept one type of connection, or multiply configured to accept various types of physical and communication connections, common or proprietary, such as USB, FireWire, Thunderbolt, or PCIe. The peripheral device connection interface 818 may also be coupled to a similarly configured peripheral device connection port (not shown). The computing device 230 may also include one or more output devices 814, such as speakers for providing audio outputs, a display for providing visual outputs, or a combination thereof. The computing device 230 may also include a housing 820, constructed of a plastic, metal, or a combination of materials, for containing all or some of the components discussed herein. The computing device 230 may include a power source 822 coupled to the processor 801, such as a permanent battery or a disposable or rechargeable battery. A rechargeable battery may also be coupled to the peripheral device connection interface 818 to receive a charging current from a source external to the computing device 230.

Processors (e.g., 201, 801) of non-interfering blood pressure measuring devices and computing devices suitable for use in various embodiments may be any programmable microprocessor, microcomputer or multiple processor chip or chips that can be configured by processor executable instructions (e.g., applications or software) to perform a variety of functions, including the functions of the various embodiments described above. In the various devices, multiple processors may be provided, such as one processor dedicated to wireless communication functions and one processor dedicated to running other applications. Typically, software applications may be stored in internal memory before they are accessed and loaded into the processors. The processors may include internal memory sufficient to store the application software instructions. In many devices, the internal memory may be a volatile or non-volatile memory, such as flash memory, or a mixture of both. For the purposes of this description, a general reference to memory refers to memory accessible by the processors including internal memory or removable memory plugged into the various devices and memory within the processors.

The above description has mainly addressed different embodiment methods, systems, and devices for identifying valid blood pressure measurements from an artery in a limb of a subject with a non-interfering continuous blood pressure measuring device. Various embodiment methods may start by providing a reference pulse and performing an initial measurement validation. In response to completing an initial measurement validation, various embodiment methods may adjust the reference pulse to take into prior blood pressure measurements of the subject.

In some embodiments, the device may be attached to the subject without any initial measurement validation being performed. In some embodiments, the device may use previous blood pressure measurements to adjust and/or update the initial measurement validation. In some embodiments, if not enough data points are collected to accurately identify valid blood pressure measurements, one or more of the various method operations described above may be performed or repeated.

In various embodiments, the non-interfering measuring device may be attached to a subject without any initial measurement validation. After a certain amount of time has passed, the device may be completely calibrated and start recording measured values of pressure in a database. Prior to being completely calibrated, the device need not record any values of pressure in the database, or maybe record values of pressure in a database, but mark them with an insecurity factor.

In various embodiments, the non-interfering measuring device may be programmed with an initial measurement validation or with an initial set of parameters, which are statistically close to a large number of subjects. This initial "rough" measurement validation may then be adapted via adaptation algorithms over time. In another embodiment, the initial "rough" measurement validation may be determined by matching a number of physical parameters of the subject to a database of test subjects and choosing the parameters of the test subject that are closest to the subject.

The foregoing method descriptions and the process flow diagrams are provided merely as illustrative examples and are not intended to require or imply that the operations of various embodiments must be performed in the order presented. As will be appreciated by one skilled in the art, the order of operations in the foregoing embodiments may be performed in more than one order. Words such as "thereafter," "then," "next," etc. are not intended to limit the order of the operations; these words are simply used to guide the reader through the description of the methods. Further, any reference to claim elements in the singular, for example, using the articles "a," "an," or "the" is not to be construed as limiting the element to the singular.

While the terms "first" and "second" are used herein, for example to describe electrodes or other elements, such identifiers are merely for convenience and are not meant to limit various embodiments to a particular order, sequence, type of network or carrier.

The various illustrative logical blocks, modules, circuits, and algorithm operations described in connection with the embodiments disclosed herein may be implemented as electronic hardware, computer software, or combinations of both. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the various embodiments.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), an FPGA or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

The functions in the various embodiments may be implemented in hardware, software, firmware, or any combination thereof. If implemented in software, the functions may be stored as one or more instructions or code on a non-transitory computer-readable medium or non-transitory processor-readable medium. The operations of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

Various embodiments include methods, devices, and systems for calibrating a blood pressure measuring device that may provide a direct substitute for current cuff-based measuring devices. Devices in accordance with various embodiments may be incorporated into articles worn by a subject or remaining in contact with the subject for continuous calibration over extended periods. In addition, the devices in accordance with various embodiments may avoid interference with the arterial measurements being taken.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the present invention is not intended to be limited to the embodiments shown herein but is to be accorded the widest scope consistent with the following claims and the principles and novel features disclosed herein.

What is claimed is:

1. A method of measuring blood pressure using a non-interfering blood pressure measuring device, comprising:
    receiving, from one or more arterial measurement sensors, a pulse waveform representing arterial pressure as a function of time for each pulse of a series of blood pressure pulses, wherein the series of blood pressure pulses are correlated to arterial distension at a measurement location of the one or more arterial measurement sensors on a subject's body;
    receiving, from one or more elevation sensors, one or more elevations of the measurement location;
    identifying, by a processor, at least one pulse in the series of blood pressure pulses that represents a transitional pulse based on one or more characteristics of the at least one pulse being indicative of a change in pulse shape; and
    determining, by the processor, a diastolic blood pressure based on the at least one identified pulse and at least one elevation from the one or more elevations that correspond to the at least one identified pulse.

2. The method of claim 1, wherein the series of blood pressure pulses are measured while a limb of the subject is raised from at or below a heart level of the subject to above the heart level.

3. The method of claim 1, wherein the one or more characteristics of the at least one pulse comprises: amplitude, pulse shape, or any combination thereof.

4. The method of claim 1, wherein identifying at least one pulse in the series of blood pressure pulses that represents the transitional pulse comprises identifying the at least one pulse in the series of blood pressure pulses with an amplitude that is a predetermined fraction of a maximum pulse amplitude.

5. The method of claim 1, wherein identifying at least one pulse in the series of blood pressure pulses that represents the transitional pulse comprises comparing pulse shapes of each pulse in the series of blood pressure pulses to a mean pulse shape and identifying the transitional pulse within the series of blood pressure pulses based on the comparison of pulses shapes of each pulse to the mean pulse shape.

6. The method of claim 1, wherein identifying at least one pulse in the series of blood pressure pulses that represents the transitional pulse comprises identifying one or more pulses within the series of blood pressure pulses having an oscillatory pulse shaped diastolic tail immediately preceded by an earlier pulse having a near exponential decay shaped diastolic tail.

7. The method of claim 1, wherein identifying at least one pulse in the series of blood pressure pulses that represents the transitional pulse comprises identifying one or more pulses within the series of blood pressure pulses having a kink in a diastolic tail of an individual pulse, wherein the kink meets a threshold deviation from a predetermined pulse shape.

8. The method of claim 1, wherein the one or more arterial measurement sensors comprises a non-interfering measuring device.

9. The method of claim 1, further comprising:
    applying a constant counter pressure, below a diastolic pressure of the subject, at the measurement location during the series of blood pressure pulses.

10. The method of claim 1, wherein the one or more elevation sensors include an elevation sensor selected from the group consisting of an inertial sensor, a barometer, a magnetic near-field device, a visual inertial odometer, a global navigation satellite system (GNSS) based sensor, and a wireless local area network (WLAN) based sensor.

11. A blood pressure measuring device, comprising:
    one or more arterial measurement sensors configured to measure arterial distension when positioned at a measurement location on a subject's body;
    one or more elevation sensors configured to measure elevations of the measurement location; and
    a processor coupled to the one or more arterial measurement sensors and the one or more elevation sensors, and configured to:
        determine based on measurements of arterial distension by the one or more arterial measurement sensors a pulse waveform representing an arterial pressure as a function of time for each pulse of a series of blood pressure pulses;
        receive, from the one or more elevation sensors, one or more elevations of the measurement location;
        identify at least one pulse in the series of blood pressure pulses that represents a transitional pulse based on one or more characteristics of the at least one pulse being indicative of a change in pulse shape; and
        determine a diastolic blood pressure based on the at least one identified pulse and at least one elevation from the one or more elevations that correspond to the at least one identified pulse.

12. The blood pressure measuring device of claim 11, wherein the processor is configured to identify the at least one pulse in the series of blood pressure pulses that represents the transitional pulse by identifying at least one pulse in the series of blood pressure pulses with an amplitude that is a predetermined fraction of a maximum pulse amplitude.

13. The blood pressure measuring device of claim 11, wherein the processor is further configured to identify at least one pulse in the series of blood pressure pulses that represents the transitional pulse by the one or more characteristics of the at least one pulse, wherein the one or more characteristics of the at least one pulse comprises: amplitude, pulse shape, or any combination thereof.

14. The blood pressure measuring device of claim 11, wherein the processor is configured to identify at least one pulse in the series of blood pressure pulses that represents the transitional pulse by comparing pulse shapes of each pulse in the series of blood pressure pulses to a mean pulse shape and identifying the transitional pulse within the series of blood pressure pulses based on the comparison of pulses shapes of each pulse to the mean pulse shape.

15. The blood pressure measuring device of claim 11, wherein the processor is configured to identify at least one pulse in the series of blood pressure pulses that represents the transitional pulse by identifying one or more pulses within the series of blood pressure pulses having an oscillatory pulse shaped diastolic tail immediately preceded by an earlier pulse having a near exponential decay shaped diastolic tail.

16. The blood pressure measuring device of claim 11, wherein the processor is configured to identify at least one pulse in the series of blood pressure pulses that represents the transitional pulse by identifying one or more pulses within the series of blood pressure pulses having a kink in a diastolic tail of an individual pulse, wherein the kink meets a threshold deviation from a predetermined pulse shape.

17. The blood pressure measuring device of claim 11, wherein the one or more arterial measurement sensors comprise a non-interfering measuring device configured to measure changes in distension of an artery without interfering with the arterial pressure at the measurement location during the series of blood pressure pulses.

18. The blood pressure measuring device of claim 11, further comprising:
at least one counter pressure device selected from the group consisting of a patch, band, sleeve, and cuff configured to apply a constant counter pressure, below a diastolic pressure of the subject, wherein the at least one counter pressure device is configured to apply the constant counter pressure at the measurement location during the series of blood pressure pulses.

19. The blood pressure measuring device of claim 11, wherein the one or more elevation sensors include an elevation sensor selected from the group consisting of an inertial sensor, a barometer, a magnetic near-field device, a visual inertial odometer, a global navigation satellite system (GNSS) based sensor, and a wireless local area network (WLAN) based sensor.

20. A blood pressure measuring device, comprising:
one or more arterial measurement sensors configured to measure arterial distension when positioned at a measurement location on a subject's body;
one or more elevation sensors configured to measure elevations of the measurement location;
means for receiving, from the one or more arterial measurement sensors, a pulse waveform representing an arterial pressure as a function of time for each pulse of a series of blood pressure pulses, wherein the series of blood pressure pulses are correlated to arterial distension at the measurement location of the one or more arterial measurement sensors on the subject's body;
means for receiving, from the one or more elevation sensors, one or more elevations of the measurement location;
means for identifying at least one pulse in the series of blood pressure pulses that represents a transitional pulse based on one or more characteristics of the at least one pulse being indicative of a change in pulse shape; and
means for determining a diastolic blood pressure based on the at least one identified pulse and at least one elevation from the one or more elevations that correspond to the at least one identified pulse.

21. A non-transitory processor-readable medium having stored there on processor-executable instructions configured to cause a processor of a blood pressure device to perform operations comprising:
receiving, from one or more arterial measurement sensors, a pulse waveform representing an arterial pressure as a function of time for each pulse of a series of blood pressure pulses, wherein the series of blood pressure pulses are correlated to arterial distension at a measurement location of the one or more arterial measurement sensors on a subject's body;
receiving, from one or more elevation sensors, one or more elevations of the measurement location;
identifying, by the processor, at least one pulse in the series of blood pressure pulses that represents a transitional pulse based on one or more characteristics of the at least one pulse being indicative of a change in pulse shape; and
determining, by the processor, a diastolic blood pressure based on the at least one identified pulse and at least one elevation from the one or more elevations that correspond to the at least one identified pulse.

22. The non-transitory processor-readable medium of claim 21, wherein the series of blood pressure pulses are measured while a limb of the subject is raised from at or below a heart level of the subject to above the heart level.

23. The non-transitory processor-readable medium of claim 21, wherein the one or more characteristics of the at least one pulse comprises: amplitude, pulse shape, or any combination thereof.

24. The non-transitory processor-readable medium of claim 21, wherein identifying at least one pulse in the series of blood pressure pulses that represents the transitional pulse comprises identifying the at least one pulse in the series of blood pressure pulses with an amplitude that is a predetermined fraction of a maximum pulse amplitude.

25. The non-transitory processor-readable medium of claim 21, wherein identifying at least one pulse in the series of blood pressure pulses that represents the transitional pulse comprises comparing pulse shapes of each pulse in the series of blood pressure pulses to a mean pulse shape and identifying the transitional pulse within the series of blood pressure pulses based on the comparison of pulses shapes of each pulse to the mean pulse shape.

26. The non-transitory processor-readable medium of claim 21, wherein identifying at least one pulse in the series of blood pressure pulses that represents the transitional pulse comprises identifying one or more pulses within the series of blood pressure pulses having an oscillatory pulse shaped diastolic tail immediately preceded by an earlier pulse having a near exponential decay shaped diastolic tail.

27. The non-transitory processor-readable medium of claim 21, wherein identifying at least one pulse in the series of blood pressure pulses that represents the transitional pulse comprises identifying one or more pulses within the series of blood pressure pulses having a kink in a diastolic tail of an individual pulse, wherein the kink meets a threshold deviation from a predetermined pulse shape.

28. The non-transitory processor-readable medium of claim 21, wherein the one or more arterial measurement sensors comprises a non-interfering measuring device configured to measure changes in distension of an artery without interfering with the arterial pressure at the measurement location during the series of blood pressure pulses.

29. The non-transitory processor-readable medium of claim 21, wherein the one or more elevation sensors include an elevation sensor selected from the group consisting of an inertial sensor, a barometer, a magnetic near-field device, a visual inertial odometer, a global navigation satellite system (GNSS) based sensor, and a wireless local area network (WLAN) based sensor.

* * * * *